(12) United States Patent
Kuo et al.

(10) Patent No.: US 6,537,979 B1
(45) Date of Patent: *Mar. 25, 2003

(54) WATER-INSOLUBLE DERIVATIVES OF HYALURONIC ACID CROSSLINKED WITH A BISCARBODIIMIDE

(75) Inventors: Jing-Wen Kuo, Stoneham, MA (US); David A. Swann, Lexington, MA (US); Glenn D. Prestwich, Harbor, NY (US)

(73) Assignees: Research Foundation of State University of New York, Albany, NY (US); Anika Therapeutics, Inc., Woburn, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/540,716

(22) Filed: Mar. 31, 2000

Related U.S. Application Data

(62) Division of application No. 09/028,414, filed on Feb. 24, 1998, now Pat. No. 6,096,727, which is a division of application No. 08/567,563, filed on Dec. 5, 1995, now Pat. No. 6,013,679, which is a division of application No. 08/292,478, filed on Aug. 18, 1994, now Pat. No. 5,502,081, which is a division of application No. 07/920,698, filed on Jul. 28, 1992, now Pat. No. 5,356,883, which is a continuation-in-part of application No. 07/809,399, filed on Dec. 18, 1991, now abandoned, which is a division of application No. 07/388,578, filed on Aug. 1, 1989, now abandoned.

(51) Int. Cl.$^7$ .......................... A61K 31/715; A61K 9/70
(52) U.S. Cl. .......................... 514/54; 536/53; 536/55.1; 536/55.2; 536/55.3; 536/123.1; 536/124; 514/777
(58) Field of Search .................. 536/53, 55.1, 55.2, 536/55.3, 123.1, 124; 514/54, 777

(56) References Cited

U.S. PATENT DOCUMENTS

| | | | |
|---|---|---|---|
| 4,280,954 A | 7/1981 | Yannas et al. | 260/123.7 |
| 4,582,865 A | 4/1986 | Balazs et al. | 524/29 |
| 4,703,108 A | 10/1987 | Silver et al. | 530/356 |
| 4,713,448 A | 12/1987 | Balazs et al. | 536/55.1 |
| 4,937,270 A | 6/1990 | Hamilton et al. | 514/777 |
| 4,973,493 A | 11/1990 | Guire | 427/2 |
| 5,017,229 A | 5/1991 | Burns et al. | 514/777 |
| 5,128,326 A | 7/1992 | Balazs et al. | 514/54 |
| 5,527,893 A | 6/1996 | Burns et al. | 514/53 |
| 5,690,961 A | 11/1997 | Nguyen | 424/488 |
| 6,096,728 A | 8/2000 | Collins et al. | 514/62 |

FOREIGN PATENT DOCUMENTS

| | | |
|---|---|---|
| EP | 0416250 | 3/1991 |
| WO | 86/00912 | 2/1986 |
| WO | 89/02445 | 3/1989 |
| WO | 90/09401 | 8/1990 |
| WO | 92/20349 | 11/1992 |

OTHER PUBLICATIONS

Jing–wen Kuo, "Synthesis and Properties of Hyaluronic Acid Modified by Designed Carbodiimides" Ph.D. Dissertation SUNY Stony Brook, 1989.

Kuo, Jing–wen, "Syntheses and Properties of Hyaluronic Acid Modified by Designed Carbodiimides," *Dissertation Abstracts International*, 50(12):5626 (1990). Month Not Available.

Beuvery, E.C., et al., "Analytical, Toxicological and Immunological Consequences of the Use of N–Ethyl–N'–(3–Dimethylaminopropyl) Carbodiimide as Coupling Reagent for the Preparation of Meningococcal Group C Polysaccharide–Tetanus Toxoid Conjugate as Vaccine for Human Use," *Develop. biol. Standard.*, 63:117–128 (1986).

Pouyani, T., et al., "Solid–State NMR of N–Acylureas Derived from the Reaction of Hyaluronic Acid with Isotopically–Labeled Cabodiimides," *J. Am. Chem. Soc.*, 114:5972–5976 (1992).

Kuo, J., et al., "Chemical Modification of Hyaluronic Acid by Carbodiimides," *Bioconjugate Chem.*, 2(4):232–241 (1991).

*Primary Examiner*—James O. Wilson
*Assistant Examiner*—Devesh Khare
(74) *Attorney, Agent, or Firm*—Hamilton, Brook, Smith & Reynolds, P.C.

(57) ABSTRACT

This invention describes a method for preparing water-insoluble biocompatible gels, films and sponges by reacting hyaluronic acid, or a salt thereof, with a carbodiimide in the absence of a nucleophile or a polyanionic polysaccharide. The water-insoluble gels, films and sponges of this invention may be used as surgical aids to prevent adhesions of body tissues and as drug delivery vehicles.

12 Claims, No Drawings

WATER-INSOLUBLE DERIVATIVES OF HYALURONIC ACID CROSSLINKED WITH A BISCARBODIIMIDE

RELATED APPLICATIONS

This application is a divisional of U.S. Ser. No. 09/028,414 filed on Feb. 24, 1998, U.S. Pat. No. 6,096,727, which is a divisional of U.S. Ser. No. 08/567,563 filed on Dec. 5, 1995, U.S. Pat. No. 6,013,679, which is a divisional of U.S. Ser. No. 08/292,478 filed on Aug. 18, 1994, U.S. Pat. No. 5,502,081, which is a divisional of U.S. Ser. No. 07/920,698 filed on Jul. 28, 1992, U.S. Pat. No. 5,356,883, which is a continuation-in-part of U.S. Ser. No. 07/809,399 filed on Dec. 18, 1991 now ABN, which is a divisional of U.S. Ser. No. 07/388,578 filed on Aug. 1, 1989 now ABN, the entire teachings of which are incorporated herein by reference.

FIELD OF THE INVENTION

The present invention relates to biocompatible gels, films and sponges formed by chemically modifying hyaluronic acid.

BACKGROUND OF THE INVENTION

Hyaluronic acid ("HA") is a naturally occurring linear polysaccharide composed of alternating disaccharide units of N-acetyl-D-glucosamine and D-glucuronidic acid joined by alternating $\beta 1 \rightarrow 4$ glucosaminidic bonds, so that the repeating unit is $(1\rightarrow 4)$-$\beta$-D-GlcA-$(1\rightarrow 3)$-$\beta$-D-GlcNAc. The disaccharide unit of hyaluronic acid, or a salt thereof, may be represented in the following way:

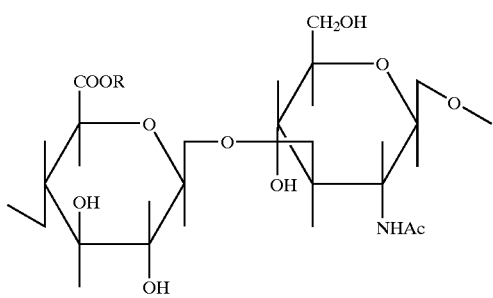

(I)

wherein Ac represents acetate and R represents hydrogen (in the case of the acid) or the cation of a salt (in the case of a salt). Preferably, the cation is an alkali metal cation, most preferably sodium ion. Hereinafter, formula I above shall be referred to in the following way:

(II)

wherein R is as defined above and B has the obvious meaning ascribed to it.

HA is widely distributed in animal tissues, present in high concentrations in synovial fluid and the vitreous body of the eye, and in connective tissues of rooster comb, umbilical cord, and dermis. The molecular weight of hyaluronic acid isolated from natural sources generally falls within the range of about $6 \times 10^4$ to about $1.2 \times 10^7$ daltons. Naturally occurring HA does not give a foreign body reaction when implanted or injected into a living body and it has excellent biocompatibility.

As used herein, the term "HA" means hyaluronic acid and any of its: hyaluronate salts, including, but not limited to, sodium hyaluronate (the sodium salt), potassium hyalurdnate, magnesium hyaluronate, and calcium hyaluronate.

HA, in chemically modified form, is useful as a surgical aid, to prevent adhesions or accretions of body tissues during the post-operation period. The modified HA composition (e.g., gel or film) is injected or inserted into the locus between the tissues that are to be kept separate to inhibit their mutual adhesion.

Chemically modified HA is also useful for controlled release drug delivery. Sparer, R.V. et al., 1983, Chapter 6, pp. 107–119, in T. J. Roseman et al., *Controlled Release Delivery Systems*, (Marcel Dekker, Inc., New York), describe the sustained release of chloramphenicol covalently attached to hyaluronic acid via ester linkage, either directly or in an ester complex including an alanine bridge as an intermediate linking group.

The literature describes two general approaches for chemically modifying HA to reduce its water solubility and diffusibility in vivo: (a) cross-linking HA by bifunctional chemical reagents and (b) coupling HA by monofunctional reagents.

Divinyl sulfone, bisepoxides, formaldehyde, and bishalides are bifunctional reagents which have been used to cross-link HA to produce highly swollen gels or virtually insoluble, plastic materials, depending upon the degree of cross-linking. Balazs, E.A. and Leshchiner, A., U.S. Pat. No. 4,582,865, describe the use of divinyl sulfone in an alkaline medium to cross-link HA. Balazs, E.A., Leshchiner, A., U.S. Pat. No. 4,713,448, describe a chemically modified HA preparation characterized by the presence of aldehyde cross-linking groups, such as formaldehyde, covalently bonded to the HA chains. Maelson, T. and Lindqvist, B. P., PCT Application WO-86-79A1, describe a method of preparing crosslinked gels of HA by reaction with a phosphorus-containing agent. De Belder, A. M. and Maelson, T., PCT Application WO-86 00912, describe a slowly-degradable gel, for preventing tissue adhesions following surgery, prepared by cross-linking a carboxyl-containing polysaccharide with a bi- or poly-functional epoxide.

There are other reactive bi- or polyfunctional agents, which have been proposed for preparing cross-linked gels of HA having reduced water solubility. For example, Balazs et al., U.S. Pat. No. 4,582,865, suggest that divinyl sulfone may be used to prepare cross-linked gels of HA having reduced water solubility. In addition, Balazs et al., U.K. Patent Application No. A4 20 560, suggest that agents such as formaldehyde, dimethylolurea, dimethylolthylene, ethylene oxide, polyaziridine, and polyisocyanate can be used to prepare cross-linked gels of HA having reduced water solubility.

Other approaches used to render HA compositions less water soluble by cross-linking the HA include modifying HA by attaching cysteine residues to the HA via amide bonds and then cross-linking the cysteine-modified HA by forming disulfide bonds between the attached cysteine residues. The cysteine-modified HA was itself water soluble and became water insoluble only upon cross-linking by oxidation to the disulfide form. Sparer, R. V. et al., 1983, chapter 6, pp. 107–119, in T. J. Roseman et al., *Controlled Release Delivery Systems* (Marcel Dekker, Inc., New York).

Coupling reactions have also been shown to alter the properties of HA. For example, extensive esterification of HA with monofunctional organic halides can produce water-insoluble films. Della Valle, F. and Romeo, A., European Patent Application 87308863.8.

Danishefsky, I. et al., *Carbohydrate Res.* 16: 199–205 (1971), describe modifying a mucopolysaccharide by converting the carboxyl groups of the mucopolysaccharide into substituted amides by reacting the mucopolysaccharide with an amino acid ester in the presence of 1-ethyl-3-(3-dimethyliaminopropyl) carbodiimide hydrochloride ("EDC") in an aqueous solution. The authors reacted glycine methyl ester with a variety of mucopolysaccharides, including HA. Daniskefsky et al. reported that the resulting products were water soluble. That is, they would rapidly dissolve in water or in an aqueous solution such as is encountered between body tissues.

Amidation reactions of HA and monofunctional amines catalyzed by carbodiimides have been shown to decrease water solubility. Hamilton et al., U.S. Pat. No. 4,937,270, describe a method for making a water-insoluble biocompatible gel by activating HA with a carbodiimide then reacting the activated HA with a nucleophile (e.g., an amine). In the presence of a primary amine as nucleophile, the O-acylisourea formation is followed by a nucleophilic attack, forming an amide linkage between the amine and the carboxylic acid.

Others, have shown that when a mixture of HA and other polyanionic polysaccharides react with a carbodiimide, a water-insoluble gel is formed. Burns et al., U.S. Pat. No. 5,017,229, describe a method of making a water-insoluble biocompatible gel by reacting HA another polyanionic polysaccharide and a carbodiimide.

SUMMARY OF THE INVENTION

The present invention is directed to biocompatible gels, films, and sponges formed by chemically modifying HA. In particular, the invention features water-insoluble biocompatible gels, films and sponges and methods for making such gels, films and sponges. The inventors have discovered that by reacting HA, or a salt thereof, with a monocarbodiimide or a biscarbodiimide, a stable HA acylurea may be made as a gel, film or sponge having decreased water solubility. This is chemically different from the HA amide product made by the carbodiimide activation of HA followed by a nucleophilic attack by a nucleophile such as an amine.

In a preferred embodiment, the reaction steps include providing an aqueous mixture of HA, or a salt thereof, adjusting the pH of the mixture to between 4.0 and 6.0 by the addition of an acid, and then reacting the aqueous HA solution with a carbodiimide, the reacting step taking place in the absence of a primary amine as nucleophile or a polyanionic polysaccharide (other than HA). Preferably, the HA solution has a concentration of between about 0.1% and about 5%; the acid includes hydrochloric acid; the carbodiimide is either a soluble monocarbodiimide or biscarbodiimide; and the molar equivalent ratio of the carbodiimide to the HA is equal to or greater than 5%.

The invention also features water-insoluble biocompatible films and sponges and methods for preparing the films and sponges. The water-insoluble film is prepared by producing a water-insoluble biocompatible gel according to the procedure described above, and then precipitating, washing and drying the modified HA polymer. The precipitated material is resuspended in water, poured into a mold having a desired shape, and air dried. Alternatively, a film may be prepared by drying the gel or compressing the gel under conditions which allow water to escape from the gel.

The water-insoluble biocompatible sponge is prepared by producing a water-insoluble biocompatible gel according to the procedure described above, and then precipitating, washing and drying the modified HA. The precipitated material is resuspended in about 100–200 volumes of water and then freeze-dried.

In another embodiment, this invention is directed to water-insoluble biocompatible gels, films and sponges which can be used as surgical aids to separate healing tissues or to prevent post-operative adhesion between healing tissues during the healing process. The surgical aids of the invention are introduced between or among the tissues, either during surgery or post-operatively. They must remain in place and prevent tissue contact for a long enough time so that when the gel, film or sponge disperses or degrades and the tissues do come into contact, they will no longer have a tendency to adhere.

The films, gels and sponges of the invention can be prepared in colored form, by including a dye or stain in the reaction mixture. Colored films, gels and sponges can be more easily seen when in place or during placement, making them easier to handle during surgical procedures than colorless ones.

In yet another embodiment, this invention is directed to drug delivery systems having a pharmaceutically-active substance, such as a therapeutic drug, which covalently bonds to, or non-covalently interacts with, the modified HA polymer of the invention. The non-covalent interactions include ionic and hydrophobic interactions in which the drug is dispersed within the gel, film or sponge. In both cases, the modified HA functions as a vehicle which provides the controlled release of a drug from the system.

Any substance which has biological or pharmaceutical activity and which is normally considered to be a drug can be used as the drug component in the delivery systems of the invention. The choice of the substance will depend upon the specific use of the drug delivery system.

A "water-insoluble" gel, film or sponge of the invention, as that phrase and like terms are used herein, is one which is heterogeneous when suspended in a sufficient amount of water and which can form two layers when subjected to low speed centrifugation at room temperature for about 30 minutes at about 1000 g.

A "biocompatible" substance, as that term is used herein, is one that has no medically unacceptable toxic or injurious effects on biological function.

A "nucleophile," as that term is used herein, is any molecule possessing an electron rich functional group (such as a primary amine).

A "polyanionic polysaccharide," as that term is used herein, is a polysaccharide other than HA containing more than one negatively charged groups, e.g., carboxyl groups.

"cross-linking agent," as that phrase is used herein, is a molecule containing two or more functional groups that can react with HA.

A "film," as that term is used herein, means a substance formed by compressing a gel or by allowing or causing a gel to dehydrate, and any gel of the invention may be formed into such a film.

A "sponge," as that term is used herein, means a substance formed by freeze-drying a gel, and any gel of the invention may be formed into such a sponge.

"Room temperature," as that phrase is used herein, includes temperatures in the range of from about 20° C. to about 25° C.

Other objects, features and advantages of this invention will be apparent to those skilled in the art from the following detailed description of preferred embodiments.

DETAILED DESCRIPTION OF THE PREFERRED EMBODIMENTS OF THE INVENTION

This invention is directed to water-insoluble derivatives of hyaluronic acid and their methods of preparation. This invention is based on the discovery that a biocompatible gel, film or sponge having decreased water solubility can be prepared by reacting hyaluronic acid, or a salt thereof, with a carbodiimide in the absence of a nucleophile or polyanionic polysaccharide (other than HA).

The insoluble gels of this invention are made in the following way: HA is dissolved in water, and the pH of the resulting aqueous mixture is adjusted to between about 4.0 and 6.0; the dissolved HA is reacted with a carbodiimide in a sufficient molar equivalent ratio with the HA to produce a water insoluble biocompatible gel and without the presence of a nucleophile (e.g. an amine) or polyanionic polysaccharide other than HA; the reaction mixture is stirred for two hours at room temperature; and the end product is precipitated with ethanol, dried and resuspended in water.

A preferred method of making the gels, films, and sponges of the invention will now be described in greater detail. A sample of HA or a salt of hyaluronic acid, such as sodium hyaluronate, is dissolved in water to make an aqueous solution. HA from any of a variety of sources can be used. As is well known, HA can be extracted from animal tissues or harvested as a product of bacterial fermentation. HA can be produced in commercial quantities by bioprocess technology, as described, for example, in Nimrod et al., PCT Publication No. WO 86/04355. Preferably, the concentration of HA in this first aqueous solution is in the range of between about 0.1% and 5% weight/weight ("w/w"), more preferably in the range of between about 0.4% and 2.6% w/w, and most preferably in the range of between about 0.4% and 0.6% w/w. The precise concentration used will vary depending on the molecular weight of the HA. At significantly lower concentrations, however, the reactions are slower and less effective. At significantly higher HA concentrations the end product may be difficult to handle due to the increase in viscosity.

The pH of the HA solution is then adjusted so that the aqueous HA solution is acidic, preferably having a pH between about 4.0 and about 6.0, more preferably between pH 4.75 and pH 5.5. Those skilled in the art will know, or will be able to ascertain with no more than routine experimentation, the most suitable pH for the reaction based on the carbodiimide which is used. At lower pH values the carbodiimides are unstable, and at higher values the reaction rate is diminished. Preferably hydrochloric acid (HCl) is added to adjust the pH, although other known acids can be used.

Once the pH of the aqueous HA solution has been adjusted, the carbodiimide can be added. Preferably, the carbodiimide is dissolved in water and added drop wise. Preferred monocarbodiimides include 1-ethyl-3-(3-dimethylaminopropyl) carbodiimide ("EDC"), cyclohexyl-B-(N-methylmorpholino) ethylcarbodiimide p-toluenesulfonate ("CMC") and, 1-(3-dimethylaminopropyl)-3-ethylcarbodiimide methiodide ("ETC"). Preferred biscarbodiimides include phenylenebis-(ethyl)-carbodiimide and 1,6-hexamethylenebis (ethylcarbodiimide). The introduction of the carbodiimide generally causes the pH to increase. However, the reaction is monitored by a pH meter and HCl is added to keep the pH of the reactionmixture between about 4.75 and 5.50. The reaction is allowed to proceed at.room temperature for about two hours.

If a colored product is desired, a solution of a biocompatible dye or stain, e.g., Coomassie™ Brilliant Blue R-250, can be admixed to the reaction mixture at this point. The resulting product will have a blue color which makes the gel, film or sponge easy to see when it is handled during surgery and when it is in place.

Sodium chloride is then added to the reaction mixture to adjust the sodium chloride concentration to 1M. Ethanol equal to three volumes of the reaction mixture is added to form a white stringy precipitate. The precipitate is soaked in clean ethanol at room temperature overnight. The next day the precipitate is dried by vacuum and then resuspended in water.

As the carbodiimide and the HA are mixed, the pH of the solution will rise. The addition of acid, as described above, will maintain an acidic pH. Films and gels with the various desired physical properties can be obtained, however, by simply allowing the pH to rise as the reaction proceeds. The ratio of the carbodiimide to the carboxyl groups of the HA is important. A ratio of at least 0.15 molar equivalents of carbodiimide to 1 molar equivalent of the carboxyl groups (15%) results in strong gels, while a ratio of 0.05:1 (5%) results in weak gels which collapse to fluid solutions over a period of days. Thus, although the ratios of carbodiimide to HA can vary over a wide range, ratios of carbodiimide to HA of equal to or greater than 5% are preferred. The more preferred ratio depends on the solubility of the carbodiimide being used and the desired physical properties of the final product. Those skilled in the art will know, or will be able to ascertain with no more than routine experimentation, the preferred molar equivalent ratio to use in any given situation.

In order to make a film, the modified HA in the reaction mixture is first precipitated with ethanol. The precipitated material is separated from the solution and then washed and dried. The dried product is then resuspended in water to make a slurry. The slurry is poured into a vessel or mold having the desired size and shape and allowed to air dry. In general, films formed by drawing mixtures poured thickly possess greater strength than films formed by drying thinner mixtures.

Alternatively, a film can be formed by compressing a gel under conditions that permit water to escape, as, for example, by compressing the gel between two surfaces, at least one of which is porous. See, for example, Maelson et al., EPO No. 0 193 510.

In order to make a sponge, the modified HA in the reaction mixture is first precipitated with ethanol. The precipitated material is separated from the solution and then washed and dried. The dried product is then resuspended in water to make a slurry. The slurry is then freeze-dried to form a modified HA sponge which is biocompatible.

The water-insoluble gels of the invention are prepared by starting with an HA composition, or any of the salts thereof, having a weight average molecular weight of from about $6\times10^4$ to about $1.2\times10^7$ daltons. The HA, or a salt thereof, is reacted with a carbodiimide in the presence of an available proton. As a first step, the carbodiimide is protonated. Then, a carboxylate anion attaches to the carbon atom of the cation formed, resulting in the formation of an O-acylisourea intermediate. The acyl group in the O-acylisourea migrates from the oxygen atom to a nitrogen atom to produce the N-acylurea derivative of hyaluronic acid. Generally, the O→N migration is incomplete, resulting in a product reaction mixture containing both N-acylurea and O-acylisourea. The mixed products may be used separately or together to prepare the biocompatible gels, films and soonces and compositions of the invention.

The reaction steps may be represented in the following way:

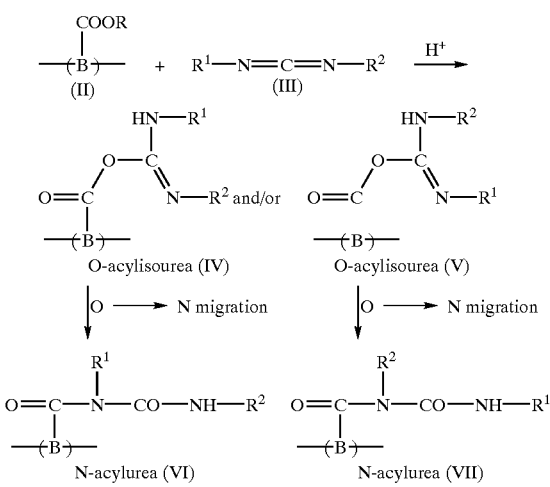

wherein R and B have the same meanings previously ascribed to them; compound III is a carbodiimide compound; and $R^1$ and $R^2$ are each independently selected from the group consisting of hydrocarbyl, substituted-hydrocarbyl, alkoxy, aryloxy, alkaryloxy and the like.

The term "hydrocarbyl" as used herein means the monovalent moiety obtained upon removal of a hydrogen atom from a parent hydrocarbon. Representative of hydrocarbyl are alkyl of 1 to 25 carbon atoms, inclusive, such as methyl, ethyl, propyl, butyl, pentyl, hexyl, heptyl, octyl, nonyl, undecyl, decyl, dodeyl, octadecyl, nonodecyl, eicosyl, heneicosyl, docosyl, trcosyl, tetracosyl, pentacosyl and the isomeric forms thereof; aryl of 6 to 25 carbon atoms, inclusive, such as phenyl, tolyl, xylyl, naphyl, biphyl, tetraphenyl and the like; aralkyl of 7 to 25 carbon atoms, inclusive, such as benzyl, phenethyl, phenpropyl, phenbutyl, phenhexyl, napthoctyl and the like; cycloalkyl of 3 to 8 carbon atoms, inclusive, such as cyclopropyl, cyclobutyl, cyclopentyl, cyclohexyl, cycloheptyl, cyclooctyl and the like; alkenyl of 2 to 25 carbon atoms, inclusive, such as vinyl, allyl, butenyl, pentenyl, hexenyl, octenyl, nonenyl, decenyl, undececyl, dodecenyl, tridecenyl, pentadecenyl, octadecenyl, pentacosynyl and isomeric forms thereof. Preferably, hydrocarbyl has 6 to 14 carbon atoms, inclusive.

The term "substituted hydrocarbyl" as used herein means the hydrocarbyl moiety as previously defined wherein one or more hydrogen atoms have been replaced with a chemical group which does not adversely affect the desired preparation of the product derivative. Representative of such groups are amino- phosphino-, quaternary nitrogen (ammonium), quarternary phosphorus (phosphonium), hydroxyl, amide, alkoxy, mercapto, nitro, alkyl, halo, sulfone, sulfoxide, phosphate, phosphite, carboxylate, carbamate groups and the like. Preferred groups are amino, amide, ester and ammonium groups.

Preferred N-acylureas and O-aclisoureas of the invention are those in which $R^1$ and/or $R^2$ are hydrocarbyl substituted with an amino group.

The term "alkoxy" as used herein means a monovalent group of the formula:

—O-alkyl wherein the alkyl preferably has 4 to 12 carbon atoms, inclusive.

The term "aryloxy" as used herein means the monovalent group of the formula:

—O-aryl wherein the aryl preferably has 6 to 10 carbon atoms, inclusive and may be substituted as described above.

The term "alkaryloxy" as used herein means the monovalent group of formula:

—O-alkylenearyl such as oxybenzyl and the like.

The schematic formulae given above to represent the preparation of N-acylurea does not illustrate the reaction or products where a biscarbodiimide is used in place of the compound III, but those skilled in the art will know, or will be able to ascertain with no more than routine experimentation, that reaction scheme.

Carbodiimides having the formula III are preferred where $R^1$ and/or $R^2$ represent more specifically alkyl, cycloalkyl, aryl or substituted forms thereof. Examples of monofunctional carbodiimides include, but are not limited to, the following:

N-methyl-N'-tert-butylcarbodiimde N,N'-diisopropylcarbodiimide N,N'-dicyclohexylcarbodiimde N,N'-ditert-butylcarbodiimde N-cyclohexyl-N'-tert-butylcarbodiimde N,N'-dibutylcarbodiimide N,N'-diisobutylcarbodiimide N-allyl-N'-propylcarbodiimde N,N'-diallycarbodiimide N,allyl-N'-cyclohexylcarbodiimide N-crotyl-N'-cyclohexylcarbodiimide N-ally-N'-(B-hydroxyethyl)carbodiimide N-methyl-N'-propylcarbodiimide N-propyl-N'tert-butylcarbodiimide N-isopropyl-N'-tert-butylcarbodiimide N-(a-dimethylaminopropyl)-N'tert-butylcarbodiimide N-(B-bromoallyl)-N'-propylcarbodiimide N-(B-bromoallyl)-N'-isopropylcarbodiimide N-(B-bromoallyl)-N'-tert-buttylcarbodiimide N-(a-dimethylaminopropyl)-N'-(B-bromoallyl) carbodiimide 1-ethyl-3-(6-benzyloxylcarbonylaminohexyl) carbodiimide 1-(3-dimethylaminopropyl)-3-(6-benzoylaminohexyl)-carbodiimide and the like.

The biscarbodiimides may be represented by those difunctional compounds having the formula:

$$R^1—N=C=N—R^2—N=C=N—R^3 \qquad \text{(VIII)}$$

wherein $R^1$ and $R^2$ have the same meanings given to them above and $R^3$ may have the same meaning as $R^1$.

Those skilled in the art will know, or will be able to ascertain with no more than routine experimentation, methods of preparing monocarbodiimides of the formula III and biscarbodiimides of the formula VIII. See, for example, the methods described in U.S. Pat. Nos. 2,946,819; 3,231,610; 3,502,722; 3,644,456; 3,972,933; 4,014,935; 4,066,629; 4,085,140; 4,096,334; and 4,137,386, all of which are incorporated herein by reference.

By appropriate selection of a particular monocarbodiimide or biscarbodiimide, or a class of such compounds, the physical properties of the biocompatible gel, film, or sponge of the invention may be tailored for advantageous use in particular applications. For example, if monofunctional carbodiimides are used, hydrophobic and/or cationic "side-arms" may be attached to the HA polymer, to prepare useful polymer carriers for therapeutic drugs.

More importantly, carbodiimide originated side-arms are covalently attached to the HA polymer chain as acylurea side-arms. Free functional groups in the side-arm (e.g., amines, amides, and esters) can be further reacted to bond with reactive therapeutic drug molecules, to obtain vehicles for delivery of therapeutic drugs, under conventional and known reaction conditions.

In carrying out the preparation of the water-insoluble products of the invention, a sufficient proportion of the carbodiirnide is reacted with the HA, or salt thereof, to obtain a polymer chain having recurring polymer chain units of formula I set forth above, interrupted by at least one disaccharide unit per HA molecule having a pendant acylurea side-arm, for example a chain unit of formula IV, V, IV or VII given above. In preferred compositions of the invention, from about 0.5 to about 30 percent of the original chain units of formula I are converted to chain units like those of formula IV, V, VI or VII. Generally an excess of the stoichometric proportion of carbodiimide is advantageous to promote the desired reaction.

Use of a biscarbodiimide reactant to prepare the water insoluble gel of the invention results in a cross-linking between adjacent hyaluronic acid molecules, since the biscarbodiimide is difunctional. These cross-linked compositions are particularly useful as biomaterials and as relatively insoluble matrices for drug delivery since the biscarbodiimide cross-linked hyaluronic acid possesses new drug binding regions which do not interfere with biocompatibility.

The biscarbodiimide cross-linked hyaluronic acid is a hydrogel. The term "hydrogel" is defined herein to mean a cross-linked macromolecular network swollen in water or biological fluids. The degree of gelation is dependent on the degree of cross-linking achieved.

The reaction conditions for HA cross-linking with a biscarbodiimide are similar to those used for HA-monocarbodiimide coupling reactions. Advantageously, the cross-linking reactions are carried out with (1) an increase of the HA concentration in the reaction mixture, and (2) a decrease of the biscarbodiimide concentration in the addition solution. This creates a condition favorable to intermolecular cross-linking versus intramolecular cross-linking.

The reactions described above may be directed to favor the formation of the N-acylurea derivatives; i.e., compounds of formula (VI) or (VII) by increasing the pH with aqueous base.

The preparative reaction may be carried out in the presence of an inert solvent, i.e., a solvent which does not enter into or otherwise adversely affect the desired course of the reaction. Representative of such solvents are water, alkanols, dimethylformamide, dimethylsulfoxide and the like. Sources of protons to carry out the preparative reaction may include dilute mineral acids such as, for example, hydrochloric acid.

The reaction proceeds satisfactorily over a wide range of temperatures, for example from −10° C. to 80° C., but the reaction is more preferably conducted at room temperature.

The progress of the reaction described above may be followed by monitoring the pH. When the pH is stabilized, the reaction is substantially complete. At the conclusion of the reaction, the desired hyaluronic acid derivative may be separated from the reaction mixture by the conventional methods of precipitation, washing and re-precipitation. The completeness of the reaction, the nature of the products and the extent of chemical modification can be determined by proton NMR on solutions of the modified hyaluronic acid solubilized in dilute NaOD to reduce viscosity.

Adhesion Prevention

This invention is also directed to methods of preparing degradable gels, films and sponges which can be used as surgical aids to prevent adhesions and accretions of body tissues.

In many instances of practical surgery, it is highly desirable to have a simple means and method for preventing direct contact between tissues and for maintaining this contact-inhibiting effect also during a post-operative or healing period. The length of the period will vary according to the actual type of surgery involved. Examples of surgical procedures in which the biocompatible gels, films and sponges of this invention may be used include, but are not limited to, operations performed in abdominal regions where it is important to prevent adhesions of the intestine or the mesentery; operations performed in the urogenital apparatus where it is important to ward off adverse effects on the ureter and bladder, and on the functioning of the oviduct and uterus; and nerve surgery operations where it is important to minimize the development of granulation tissue. In surgery involving tendons there is generally a tendency towards adhesion between the tendon and the surrounding sheath or other surrounding tissue during the immobilization period following the operation. Attempts to solve this problem by using various kinds of sutures and by means of passive movements of the tendon during the healing process have been unsuccessful.

In opthalmological surgery it is often desirable to have degradable implants at one's disposal which are to be applied in the angle of the anterior chamber of the eye for the purpose of preventing synechiae between the cornea and the iris; this applies especially in cases of reconstructions after severe damaging events. Moreover, degradable or permanent implants are often desirable for preventing adhesion after glaucoma surgery and strabismus surgery.

In one particular type of articular surgery silicone plates are surgically introduced in order to prevent accretions of cartilaginous tissue. Engkvist et al., *Scand J. Plast. Reconstr. Surg.* 14: 71–87 (1980). After 12 to 16 weeks, however, it is necessary to surgically remove the implant. Thus, the techniques presently available necessitate removal of the inserted material after a suitable period of time in all cases where this material has to be of a rigid type for the sake of securing a high degree of mechanical stability. In other cases, where mechanical stability is not a major factor, it has been customary to use non-crosslinked dextran or hyaluronic acid. But even if a substance of such high viscosity as hyaluronic acid is used for application to contact surfaces, the protection period obtained is too short to be satisfactory.

The gel, film or sponge is introduced between or among the tissues of a surgical site, either during surgery or post-operatively, to separate the healing tissues or to prevent post-operative adhesion between the healing tissues. The gels, films and sponges of this invention are particularly advantageous because they will diffuse or be degraded after a desired period of time. However, it must remain in place and prevent tissue contact for a long enough time so that when the gel, film or sponge finally disperses or degrades and the tissues do come into contact, they will no longer have a tendency to adhere. Preferably, the tissues should be separated for a period of at least about 7 days post-operatively.

The rate at which the gel, film or sponge diffuses will depend primarily on the chemical nature of the composition (including the degree of cross-linking), the extent of insolubility of the composition, and the density of the modified HA in the composition. In particular, gels, films and sponges which have a high degree of cross-linking, or which are more insoluble, or which have a higher density will diffuse at a slower rate. Preferably, the density of modified HA in the film or sponge will be in the range of from about 0.1 mg/cm$^2$ to about 10 mg/cm$^2$. The rate of diffusion required will vary according to the type of surgery involved. Those skilled in the art will know, or will be able to ascertain with no more than routine experimentation, the appropriate combination of insolubility, density and chemistry that will yield a gel, film or sponge having the desired rate of diffusion for a given situation.

Drug Delivery

The gels, films and sponges of the invention can also be used as vehicles for delivering pharmaceutically-active substances to a desired site in the body of a mammal. A pharmaceutically-active substance can be chosen which covalently bonds to the modified HA of either the gel, film or sponge of the invention to form a drug delivery system with controlled release. Alternatively, a pharmaceutically-active substance can be chosen which non-covalently interacts with the modified HA. In both cases, the drug delivery system is then infected or implanted at the locus where delivery is desired. Suitable pharmaceutically-active substances include growth factors, enzymes, therapeutic drugs, biopolymers, and biologically compatible synthetic polymers.

Those skilled in the art will appreciate that the functional carboxylic acid group of unmodified HA is sheltered by the molecule conformation, making it slow to react, if at all. The modified HA of this invention, however, is an HA acylurea which possess at least one "side-arm" or "spacer" projecting outwardly from the polymer chain. This outwardly projecting side-arm includes one or more reactive sites, depending on the monocarbodiimide or biscarbodiimide employed. The reactive site(s) include at the least a primary or secondary amino, amide, imino or ammonium group. The availability of a free amino group provides a reaction site free of steric hindrance associated with the polymer chain. This reaction site may then be used to couple the water-insoluble compositions of the invention to a therapeutic drug.

The HA polymer and its pendant side-arm may be diagramatically represented in the following way:

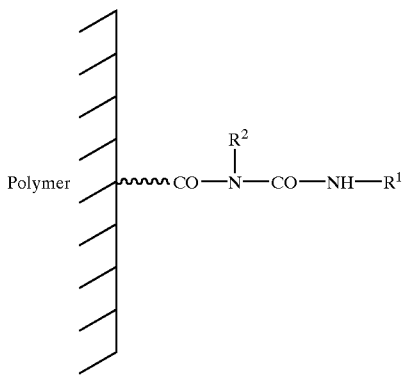

wherein R$^1$ and R$^2$ have the same meanings assignd to them previously.

There are two chemical interactions in the drug delivery systems of the invention. The first is a very stable acylurea linkage between the modified HA molecule and the monocarbodiimide or biscarbodiimide moiety. The second is a less stable linkage or interaction between the carbodiimide moiety and the therapeutic drug moiety which is more readily broken at the site of administration than the first linkage. The more stable chemical bond between the HA molecule and the carbodiimide moiety will insure the release of the therapeutic drug without the release of the carbodiimide residue, which might affect the therapeutic action of the drug.

The drug delivery system of this invention can be prepared by covalently binding the pharmaceutically-active substance to the modified HA of the gel, film or, sponge. For example, a primary amine-functionalized HA can be used as a tether for drug coupling. A carboxylate-containing anti-inflammatory drug, such as Ibuprofen (2-methyl-4-(2-methyl-propyl) benzeneacetic acid), can be converted to the corresponding N-hydroxysuccinimide (NHS) active esters, which can react with the primary amine under physiological conditions.

Peptides can also be linked to the amine tether of an amine-functionalized HA. A thiol cleavable crosslinker such as dithiobis (succinimidyl)-propionate (DSP) is first used to crosslink the amine tethers of HA. Then, the sulfhydryl groups produced through the reduction of the disulfide bonds can react with the e-amino group of lysine of the peptides through the hetierobifunctional crosslinker N-succinimidyl-3-(2-pyrlidyldithio) propionate (SPDP).

Alternatively, therapeutic drugs containing reactive functional groups (e.g., hydroxyl, carboxyl, amino) can be covalently bonded to the carbodiimide prior to reaction with HA to form hydrolysable bonds. Then, the carbodiimides which contain drugs can be attached to HA via the acylurea linkage. For example, a carboxyl containing therapeutic drug can react with a carboddimide precursor, e.g., a thiourea, bearing a pendant amine or hydroxyl group to tether the drug through an enzymatically labile amide or ester linkage. The resulting thiourea may then be converted to the corresponding carbodiimide. Upon reaction of the carbodiimide with the hyaluronic acid, a drug delivery system is obtained without further reactions.

Delivery is also related to the degradation of the gel, film or sponge as a result of numerous metabolic processes taking place in vivo. The degradation process is usually slower than diffusion which provides the delivery of a drug via delivery systems in which the drug non-covalently interacts with the modified HA of the gel, film or sponge vehicle (see below). By choosing the concentraiton of HA, one can control the rate of degradation or diffusion and, thus, the rate of drug delivery.

Other types of drug delivery systems according to the present invention include those in which a drug is dispersed within the water-insoluble gel, film or sponge. As used herein, the term "dispersed" shall refer to ionic and hydrophobic interactions between the drug and the modified HA. For example, by selection of appropriate carbodiimides, such as EDC, a cationic moiety can be immobilized to HA polymer chains. This cationic site may serve as a non-covalent, ionic binding site for anionic substances such as non-steroidal anti-inflammatory drugs (e.g., naprosyn).

A hydrophobic interaction between the drug and the modified HA can occur when, by appropriate selection of the carbodiimide, the hydrophilic HA is controllably converted in character to include a hydrophobic entity which is receptive to further interaction with a therapeutic drug having a hydrophobic moiety. Suitable drugs include fatty acid derivatives, steriods (e.g., dexamethasone) and their analogs, and other drugs with significant hydrophobicity.

The modification of the HA by reaction with a carbodiimide does not adversely degrade the polymer. At a low degree of chemical modification, the properties of viscoelasticity may be retained to produce a soluble product. One skill in the art will know, or will be able to ascertain with no more than routine experimentation, the degree of chemical modification necessary to yield an insoluble gel. Unexpectedly, the intrinsic viscosity is increased in the derivative compound. This may be advantageous in some cases where a high viscosity is desired for implanting a therapeutic drug.

A "therapeutic drug," as that term is used herein, includes:
(i) Compounds and compositions recognized in the official United States Pharmacopoeia, the official Homeopathic Pharmacopoeia of the United States, or the official National Formulary, or any supplement of any of them;
(ii) Compounds and compositions intended for use in the diagnosis, cure, mitigation, treatment, or prevention of disease in man or other animals; and
(iii) Compounds and compositions (other than food) intended to affect the structure or any function of the body of man or other animals.

Examples of classes of therapeutic drugs include steroidal and non-steroidal anti-inflammatory drugs, hormones and any synthetic analogues and pharmaceutically-active fragments thereof.

Therapeutic drugs which are suitable for use in the delivery system of the invention may be fat soluble, water-soluble, anionic or cationic, as long as they can interact with a group on the carbodiimide residue to form either the covalent or ionic bonds or hydrophobic interactions described above.

The delivery system of the invention is particularly well-suited for administering growth factors (e.g., interleukins, prostaglandins, thromboxanes, leukotrienes and cytokines), steroidal and non-steroidal contraceptive agents, antibiotics (e.g., penicillin, streptomycin and lincomycin), analgesics, sedatives, barbiturates, aminoalkylbenzenes, catecholamines, narcotics, narcotic antagonists, anti-neoplastic agents and anticoagulants (e.g., heparin and heparin sulfate).

The drug delivery products of the invention can be administered to a mammal, including humans, in pharmaceutically-acceptable dosage forms, with or without the use of pharmaceutically-acceptable carriers. Dosage forms include, but are not limited to, intravenous, intra-articular, sub-cutaneous, oral and topical administration forms.

The drug concentration can be varied over very broad limits and preferably should be chosen depending on the solubility of the drug, its pharmaceutical activity, and the effect desired.

The principal advantage of these drug delivery systems is provided by the fact that the modified HA has outstanding biocompatibility and does not cause any complications when used in humans. By being combined with other materials like polymeric substrates, sponges, gauze, etc., the drug delivery products according to the invention can be used in numerous medical devices including contraceptive devices, wound dressings, drug delivery patches, etc.

In mammals, the majority of free HA in the body is taken up in the lymphatic system, this is especially true for the higher molecular weight HA. The HA circulating in the human body has a medium molecular weight in the range of $1.4 \times 10^5$ to $2.7 \times 10^5$ and is taken up by liver endothelial cells. HA with a molecular weight less than $2.5 \times 10^4$ is within the filtration limit of human kidneys and is excreted in urine. Accordingly, one advantageous composition for the treatment of certain neoplastic disease is an intravenous administration of an acylurea-cytotoxin combination. Lymphocyte receptors will take up and bind the combination, releasing the therapeutic drug at the site of neoplastic incursions. Also, by the selection of HA having an appropriate molecular weight, the kidneys can be targeted for drug administration.

EXAMPLES

The invention is described in more detail in the following examples. These examples are given by way of illustration and are not intended to limit the invention in any way.

Examples 1–34 describe experiments in which monocarbodiimides and biscarbodiimides were reacted with HA at various molar equivalent ratios. The molecular weight of the HA used in Examples 10–30 was approximately $1.2 \times 10^6$ daltons, and the molecular weight of the HA used in Examples 31–34 was between about $1.5 \times 10^6$ and $2.0 \times 10^6$ daltons.

Example 1

This example illustrates that a molar equivalent ratio of EDC/HA of 3.05% yields a viscous solution.

A solution of HA (5.5 mg/ml; 0.281 mequiv) was brought to pH 4.75 using 0.1N HCl. Then, a solution of EDC (1.67 mg; 0.0086 mmol) was added to the HA solution. The reagents were mixed for 2 hours at room temperature. The concentration of sodium chloride was then adjusted to 1M. Ethanol equal to three volumes of the reaction mixture was added to precipitate the chemically modified HA. The precipitate was separate from the solution, washed, and dried. A viscous and homogeneous solution was formed when water was added to the precipitate.

Example 2

This example illustrates that a molar equivalent ratio of EDC/HA of 4.94% yields a water-insoluble gel.

A solution of HA (5.5 mg/ml; 0.281 mequiv) was brought to pH 4.75 using 0.1N HCl. Then, EDC (2.72 mg; 0.0139 mmol) was added to the HA solution. The reagents were mixed for 2 hours at room temperature. The concentration of sodium chloride was then adjusted to 1% w/v. Ethanol equal to three volumes of the reaction mixture was added to precipitate the chemically modified HA. The precipitate was separated from the solution, washed, and dried. When the precipitate was resuspended in water it formed an insoluble gel.

Example 3

This example illustrates that a molar equivalent ratio of EDC/HA of 9.77% yields a water-insoluble gel.

A solution of HA (5.5 mg/ml; 0.283 mequiv) was brought to pH 4.75 using 0.1N HCl. Then, EDC (5.42 mg; 0.0277 mmol) was added. Then reaction was allowed to proceed for 2 hours at room temperature. The concentration of sodium chloride was then adjusted to 1% w/v. Ethanol equal to three volumes of the reaction mixture was added to precipitate the chemically modified HA. The precipitate was separated from the solution, washed, and dried. When the precipitate was resuspended in water it formed an insoluble gel.

Example 4

This example illustrates that a molar equivalent ratio of EDC/HA of 14.71% yields a water-insoluble gel.

A solution of HA (5.5 mg/ml; 0.281 mequiv) was brought to pH 4.75 using 0.1N HCl. Then, EDC (8.10 mg; 0.0414 mmol) was added. The reaction was allowed to proceed for 2 hours at room temperature. The concentration of sodium chloride was then adjusted to 1% w/v. Ethanol equal to three volumes of the reaction mixture was added to precipitate the chemically modified HA. The precipitate was separated from the solution, washed, and dried. When the precipitate was resuspended in water it formed an insoluble gel.

Example 5

This example illustrates that a molar equivalent ratio of EDC/HA of 19.53% yields a water-insoluble gel.

A solution of HA (5.5 mg/ml; 0.281 mequiv) was brought to pH 4.75 using 0.1N HCl. Then, EDC (10.75 mg; 0.0549 mmol) was added. The reaction was allowed to proceed for 2 hours at room temperature. The concentration of sodium chloride was then adjusted to 1% w/v. Ethanol equal to three volumes of the reaction mixture was added to precipitate the chemically modified HA. The precipitate was separated from the solution, washed, and dried. When the precipitate was resuspended in water it formed an insoluble gel.

Example 6

This example illustrates that a molar equivalent ratio of EDC/HA of 29.71% yields a water-insoluble gel.

A solution of HA (5.5 mg/ml; 0.285 mequiv) was brought to pH 4.75 using 0.1N HCl. Then, EDC (16.14 mg; 0.0839 mmol) was added to the HA solution. The reagents were mixed for 2 hours at room temperature. The concentration of sodium chloride was then adjusted to 1% w/v. Ethanol equal to three volumes of the reaction mixture was added to precipitate the chemically modified HA. The precipitate was separated from the solution, washed, and dried. When the precipitate was resuspended in water it formed an insoluble gel.

Example 7

This example illustrates that a molar equivalent ratio of EDC/HA of 38.97% yields a water-insoluble gel.

A solution of HA (5.5 mg/ml; 0.281 mequiv) was brought to pH 4.75 using 0.1N HCl. Then, EDC (21.46 mg; 0.1097 mmol) is added to the HA solution. The reagents were mixed for 2 hours at room temperature. The concentration of sodium chloride was then adjusted to 1% w/v. Ethanol equal to three volumes of the reaction mixture was added to precipitate the chemically modified HA. The precipitate was separated from the solution, washed, and dried. When the precipitate is resuspended in water it formed an insoluble gel.

Example 8

This example illustrates that a molar equivalent ratio of EDC/HA of 49.07% yields a water-insoluble gel.

A solution of HA (5.5 mg/ml; 0.281 mequiv) was brought to pH 4.75 using 0.1N HCl. Then, EDC (27.05 mg; 0.1383 mmol) was added to the HA solution. The reagents were mixed for 2 hours at room temperature. The concentration of sodium chloride was then adjusted 1% w/v. Ethanol equal to three volumes of the reaction mixture was added to precipitate the chemically modified HA. The precipitate was separated from the solution, washed, and dried. When the precipitate was resuspended in water it formed an insoluble gel.

Example 9

This example illustrates that a molar equivalent ratio of EDC/HA of 68.96% yields a water-insoluble gel.

A solution of HA (5.5 mg/ml; 0.281 mequiv) was brought to pH 4.75 using 0.1N HCl. Then, EDC (38.02 mg; 0.1943 mmol) was added to the HA solution. The reagents were mixed for 2 hours at room temperature. The concentration of sodium chloride was then adjusted to 1% w/v. Ethanol equal to three volumes of the reaction mixture was added to precipitate the chemically modified HA. The precipitate was separated from the solution, washed, and dried. When the precipitate was resuspended in water it formed an insoluble gel.

Example 10

This example illustrates that a molar equivalent ratio of EDC/HA of 97.57% yields a water-insoluble gel.

A solution of HA (5.5 mg/ml; 0.281 mequiv) was brought to pH 4.75 using 0.1N HCl. Then, EDC (53.81 mg; 0.2750 mmol) was added to the HA solution. The reagents were mixed for 2 hours at room temperature. The concentration of sodium chloride was then adjusted to 1% w/v. Ethanol equal to three volumes of the reaction mixture was added to precipitate the chemically modified HA. The precipitate was separated from the solution, washed, and dried. When the precipitate was resuspended in water it formed an insoluble gel.

Example 11

This example illustrates that a molar equivalent ratio of CMC/HA of 3.00% yields a viscous solution.

A solution of HA (5.9 mg/ml; 0.297 mequiv) was brought to pH 5.50 using 0.1N HCl. Then, CMC (3.79 mg; 0.009 mmol) was added to the HA solution. The reagents were mixed for 2 hours at room temperature. The concentration of sodium chloride was then adjusted to 1% w/v. Ethanol equal to three volumes of the reaction mixture was added to precipitate the chemically modified HA. The precipitate was separated from the solution, washed, and dried. A viscous solution was formed when water was added to the precipitate.

Example 12

This example illustrates that a molar equivalent ratio of CMC/HA of 5.07% yields a water-insoluble gel.

A solution of HA (5.9 mg/ml; 0.298 mequiv) was brought to pH 5.50 using 0.1N HCl. Then, CMC (6.40 mg; 0.015 mmol) was added to the HA solution. The reagents were mixed for 2 hours at room temperature. The concentration of sodium chloride was then adjusted to 1% w/v. Ethanol equal to three volumes of the reaction mixture was added to precipitate the chemically modified HA. The precipitate was separated from the solution, washed, and dried. When the precipitate was resuspended in water it formed an insoluble gel.

Example 13

This example illustrates that a molar equivalent ratio of CMC/HA of 11.14% yields a water-insoluble gel.

A solution of HA (5.9 mg/ml; 0.298 mequiv) was brought to pH 5.50 using 0.1N HCl. Then, CMC (14.08 mg; 0.033 mmol) was added to the HA solution. The reagents were mixed for 2 hours at room temperature. The concentration of sodium chloride was then adjusted to 1% w/v. Ethanol equal to three volumes of the reaction mixture was added to precipitate the chemically modified HA. The precipitate was separated from the solution, washed, and dried. When the precipitate was resuspended in water it formed an insoluble gel.

Example 14

This example illustrates that a molar equivalent ratio of CMC/HA of 15.18% yields a water-insoluble gel.

A solution of HA (5.9 mg/ml; 0.298 mequiv) was brought to pH 5.50 using 0.1N HCl. Then, CMC (19.20 mg; 0.045 mmol) was added to the HA solution. The reagents were mixed for 2 hours at room temperature. The concentration of sodium chloride was then adjusted to 1% w/v. Ethanol equal to three volumes of the reaction mixture was added to precipitate the chemically modified HA. The precipitate was separated from the solution, washed, and dried. When the precipitate was resuspended in water it formed an insoluble gel.

Example 15

This example illustrates that a molar equivalent ratio of CMC/HA of 20.22% yields a water-insoluble gel.

A solution of HA (5.9 mg/ml; 0.298 mequiv) was brought to pH 5.50 using 0.1N HCl. Then, CMC (25.61 mg; 0.061 mmol) was added to the HA solution. The reagents were mixed for 2 hours at room temperature. The concentration of sodium chloride was then adjusted to 1% w/v. Ethanol equal to three volumes of the reaction mixture was added to precipitate the chemically modified HA. The precipitate was separated from the solution, washed, and dried. When the precipitate was resuspended in water it formed an insoluble gel.

Example 16

This example illustrates that a molar equivalent ratio of CMC/HA of 30.36% yields a water-insoluble gel.

A solution of HA (5.9 mg/ml; 0.298 mequiv) was brought to pH 5.50 using 0.1N HCl. Then, CMC (38.41 mg; 0.091 mmol) was added to the HA solution. The reagents were mixed for 2 hours at room temperature. The concentration of sodium chloride was then adjusted to 1% w/v. Ethanol equal to three volumes of the reaction mixture was added to precipitate the chemically modified HA. The precipitate was separated from the solution, washed, and dried. When the precipitate is resuspended in water it formed an insoluble gel.

Example 17

This example illustrates that a molar equivalent ratio of CMC/HA of 40.44% yields a water-insoluble gel.

A solution of HA (5.9 mg/ml; 0.298 mequiv) was brought to pH 5.50 using 0.1N HCl. Then, CMC (51.21 mg; 0.121 mmol) was added to the HA solution. The reagents were mixed for 2 hours at room temperature. The concentration of sodium chloride was then adjusted to 1% w/v. Ethanol equal to three volumes of the reaction mixture was added to precipitate the chemically modified HA. The precipitate was separated from the solution, washed, and dried. When the precipitate was resuspended in water it formed an insoluble gel.

Example 18

This example illustrates that a molar equivalent ratio of CMC/HA of 50.68% yields a water-insoluble gel.

A solution of HA (5.9 mg/ml; 0.298 mequiv) was brought to pH 5.50 using 0.1N HCl. Then, CMC (64.01 mg; 0.151 mmol) was added to the HA solution. The reagents were mixed for 2 hours at room temperature. The concentration of sodium chloride was then adjusted to 1% w/v. Ethanol equal to three volumes of the reaction mixture was added to precipitate the chemically modified HA. The precipitate was separated from the solution, washed, and dried. When the precipitate was resuspended in water it formed an insoluble gel.

Example 19

This example illustrates that a molar equivalent ratio of CMC/HA of 70.74% yields a water-insoluble gel.

A solution of HA (5.9 mg/ml; 0.299 mequiv) was brought to pH 5.50 using 0.1N HCl. Then, CMC (89.62 mg; 0.212 mmol) was added to the HA solution. The reagents were mixed for 2 hours at room temperature. The concentration of sodium chloride was then adjusted to 1% w/v. Ethanol equal to three volumes of the reaction mixture was added to precipitate the chemically modified HA. The precipitate was separated from the solution, washed, and dried. When the precipitate was resuspended in water it formed an insoluble gel.

Example 20

This example illustrates that a molar equivalent ratio of CMC/HA of 101.16% yields a water-insoluble gel.

A solution of HA (5.9 mg/ml; 0.298 mequiv) was brought to pH 5.50 using 0.1N HCl. Then, CMC (128.03 mg; 0.302 mmol) was added to the HA solution. The reagents were mixed for 2 hours at room temperature. The concentration of sodium chloride was then adjusted to 1% w/v. Ethanol equal to three volumes of the reaction mixture was added to precipitate the chemically modified EA. The precipitate was separated from the solution, washed, and dried. When the precipitate was resuspended in water it formed an insoluble gel.

Example 21

This example illustrates that a molar equivalent ratio of ETC/HA of 3% yields a viscous solution.

A solution of HA (5.9 mg/ml; 0.290 mequiv) was brought to pH 4.75 using 0.1N HCl. Then, ETC (2.58 mg; 0.0087 mmol) was added to the HA solution. The reagents were mixed for 2 hours at room temperature. The concentration of sodium chloride was then adjusted to 1% w/v. Ethanol equal to three volumes of the reaction mixture was added to precipitate the chemically modified HA. The precipitate was separated from the solution, washed, and dried. A viscous and homgeneous solution was formed when water was added to the precipitate.

Example 22

This example illustrates that a molar equivalent ratio of ETC/HA of 5% yields a water-insoluble gel.

A solution of HA (5.9 mg/ml; 0.290 mequiv) was brought to pH 4.75 using 0.1N HCl. Then, ETC (4.3 mg; 0.0145 mmol) is added to the HA solution. The reagents were mixed for 2 hours at room temperature. The concentration of sodium chloride was then adjusted to 1% w/v. Ethanol equal to three volumes of the reaction mixture was added to precipitate the chemically modified HA. The precipitate was separated from the solution, washed, and dried. When the precipitate was resuspended in water it formed an insoluble gel.

Example 23

This example illustrates that a molar equivalent ratio of ETC/HA of 10% yields a water-insoluble gel.

A solution of HA (5.9 mg/ml; 0.290 mequiv) was brought to pH 4.75 using 0.1N HCl. Then, ETC (8.6 mg; 0.0290 mmol) was added to the HA solution. The reagents were mixed for 2 hours at room temperature. The concentration of sodium chloride was then adjusted to 1% w/v. Ethanol equal to three volumes of the reaction mixture was added to precipitate the chemically modified HA. The precipitate was separated from the solution, washed, and dried. When the precipitate was resuspended in water it formed an insoluble gel.

Example 24

This example illustrates that a molar equivalent ratio of ETC/HA of 15% yields a water-insoluble gel.

A solution of HA (5.9 mg/ml; 0.290 mequiv) was brought to pH 4.75 using 0.1N HCl. Then, ETC (12.9 mg; 0.0435 mmol) was added to the HA solution. The reagents were mixed for 2 hours at room temperature. The concentration of sodium chloride was then adjusted to 1% w/v. Ethanol equal to three volumes of the reaction mixture was added to precipitate the chemically modified HA. The precipitate was separated from the solution, washed, and dried. When the precipitate was resuspended in water it formed an insoluble gel.

Example 25

This example illustrates that a molar equivalent ratio of ETC/HA of 20% yields a water-insoluble gel.

A solution of HA (5.9 mg/ml; 0.290 mequiv) was brought to pH 4.75 using 0.1N HCl. Then, ETC (17.2 mg; 0.0580 mmol) was added to the HA solution. The reagents were mixed for 2 hours at room temperature. The concentration of sodium chloride was then adjusted to 1% w/v. Ethanol equal to three volumes of the reaction mixture was added to precipitate the chemically modified HA. The precipitate was separated from the solution, washed, and dried. When the precipitate was resuspended in water it formed an insoluble gel.

Example 26

This example illustrates that a molar equivalent ratio of ETC/HA of 30% yields a water-insoluble gel.

A solution of HA (5.9 mg/ml; 0.290 mequiv) was brought to pH 4.75 using 0.1N HCl. Then, ETC (25.8 mg; 0.0869 mmol) was added to the HA solution. The reagents were mixed for 2 hours at room temperature. The concentration of sodium chloride was then adjusted to 1% w/v. Ethanol equal to three volumes of the reaction mixture was added to precipitate the chemically modified HA. The precipitate was separated from the solution, washed, and dried. When the precipitate was resuspended in water it formed an insoluble gel.

Example 27

This example illustrates that a molar equivalent ratio of ETC/HA of 40% yields a water-insoluble gel.

A solution of HA (5.9 mg/ml; 0.290 mequiv) was brought to pH 4.75 using 0.1N HCl. Then, ETC (34.4 mg; 0.1159 mmol) was added to the HA solution. The reagents were mixed for 2 hours at room temperature. The concentration of sodium chloride was then adjusted to 1% w/v. Ethanol equal to three volumes of the reaction mixture was added to precipitate the chemically modified HA. The precipitate was separated from the solution, washed, and dried. When the precipitate was resuspended in water it formed an insoluble gel.

Example 28

This example illustrates that a molar equivalent ratio of ETC/HA of 50% yields a water-insoluble gel.

A solution of HA (5.9 mg/ml; 0.290 mequiv) was brought to pH 4.75 using 0.1N HCl. Then, ETC (43.0 mg; 0.1449 mmol) was added to the HA solution. The reagents were mixed for 2 hours at room temperature. The concentration of sodium chloride was then adjusted to 1% w/v. Ethanol equal to three volumes of the reaction mixture was added to precipitate the chemically modified HA. The precipitate was separated from the solution, washed, and dried. When the precipitate was resuspended in water it formed an insoluble gel.

Example 29

This example illustrates that a molar equivalent ratio of ETC/HA of 70% yields a water-insoluble gel.

A solution of HA (5.9 mg/ml; 0.290 mequiv) was brought to pH 4.75 using 0.1N HCl. Then, ETC (60.2 mg; 0.2028 mmol) was added to the HA solution. The reagents were mixed for 2 hours at room temperature. The concentration of sodium chloride was then adjusted to 1% w/v. Ethanol equal to three volumes of the reaction mixture was added to precipitate the chemically modified HA. The precipitate was separated from the solution, washed, and dried. When the precipitate was resuspended in water it formed an insoluble gel.

Example 30

This example illustrates that a molar equivalent ratio of ETC/HA of 100% yields a water-insoluble gel.

A solution of HA (5.9 mg/ml; 0.290 mequiv) was brought to pH 4.75 using 0.1N HCl. Then, ETC (86.0 mg; 0.2897 mmol) was added to the HA solution. The reagents were mixed for 2 hours at room temperature. The concentration of sodium chloride was then adjusted to 1% w/v. Ethanol equal to three volumes of the reaction mixture was added to precipitate the chemically modified HA. The precipitate was separated from the solution, washed, and dried. When the precipitate was resuspended in water it formed an insoluble gel.

Example 31

This example illustrates that the reaction of the biscarbodiimide p-phenylenebis-(ethyl)-carbodiimide and HA at a molar equivalent ratio of 12% yields a water-insoluble gel.

A solution of HA (404 mg; 1.01 mequiv; was brought to pH 4.75 using 0.1N HCl. Then, 12.8 mg (0.06 mmol) of p-phenylenebis-(ethyl)-carbodiimide was added to the HA solution. The reagents were mixed for 2 hours at room temperature. The concentration of sodium chloride was then adjusted to 1M. Ethanol equal to three volumes of the reaction mixture was then added and a white stringy precipitate formed. The precipitate was separated from the solution, washed, and dried. The precipitate was separated from the solution, washed, and dried. When the precipitate was resuspended in water it formed an insoluble gel that was stable in water at room temperature. The degree of cross-linking, calculated from the percentage ratio of the added carbodiimide group over the hyalurnate's carboxyl group, was 12%.

Example 32

This example illustrates that reaction of p-phenylenebis-(ethyl)-carbodiimide with HA at a molar equivalent ratio of 18% yields a water-insoluble product.

A solution of HA (4.2 mg/ml; 0.96 mequiv) was adjusted to pH 4.75 with 0.1N HCl. The biscarbodiimide solution (1.5 mg/ml in 2-propanol; 18 mg; 0.084 mmol) was then added to the HA solution. The reagents were mixed for 2 hours at room temperature. The concentration of the sodium chloride was adjusted to 1M. Ethanol equal to three volumes of the reaction mixture was added to precipitate the chemically modified HA. The precipitate was separated from the solution, washed and dried. The dried precipitate swelled in 200 volumes of water at 4° C. to form a water-insoluble gel.

Example 33

This example illustrates the preparation of a water-insoluble biocompatible sponge.

A solution of HA 4.2 mg/ml; 1.01 mequiv) was adjusted to pH 4.75 with 0.1N HCl. A solution of p-phenylenebis-(ethyl)-carbodiimide (1.5 mg/ml in 2-propanol; 8.56 mg; 0.04 mmol) was then added to the HA solution. The molar equivalent ratio of the biscarbodiimide to the HA was 0.08:1 or 8%. The reagents were mixed for 2 hours at room temperature. The concentration of the sodium chloride was adjusted to 1M. Ethanol equal to three volumes of the reaction mixture was added to precipitate the chemically-modified HA. The precipitate was separated from the solution, washed and dried. The dried precipitate was resuspended in 100 volumes of water at 4° C. to form a water-insoluble gel. The insoluble gel was then freeze-dried overnight to form a sponge.

Example 34

This example illustrates that the reaction of the biscarbodiimide 1,6-hexamethylenebis-(ethyl)-carbodiimide and HA at a molar equivalent ratio of 10% yields a water-insoluble gel.

A solution of HA (3.2 mg/ml; 1.05 mequiv) was adjusted to pH 4.75 using 0.1N HCl. The biscarbodiimide solution (2.75 mg/ml in 2-propanol; 11 mg; 0.05 mmol) was then added to the HA solution. The reagents were mixed for two hours at room temperature. The concentration of the sodium chloride was adjusted to 1M. Ethanol equal to three volumes of the reaction mixture was added to precipitate the chemically modified HA. The precipitate was separated from the solution, washed, and dried. The dried precipitate formed an insoluble gel when resuspended in water.

Example 35

The experiments described below were undertaken to evaluate the anti-adhesion properties of the water-insoluble biocompatible sponge of the invention.
Materials and Methods The experimental animal was the female Spraque-Dawley rat weighing between 225 and 250 grams. These animals were monitored for at least one week prior to surgery to insure their good health and stability. The animals were anesthetized with intraperitoncal sodium pentobarbital and their abdomens prepared for surgery. The abdominal cavity was exposed through a midline incision. On the abdominal wall overlying the cecum, a 1 cm×2 cm segment of parietal peritoneum was excised. The defect was about 0.5 cm from the midline incision with the long axis of the defect running parallel to the midline. The surface of the exposed abdominal muscle was abraded in a uniform manner. A scalpel was used to scrape the surface until a uniform abrasion was created. This defect was left exposed for 15 minutes. The proximal end of the cecum was emptied of its contents. A 2 cm×2 cm area on the anterior surface of the proximal end of the cecum was scraped with a scalpel blade to remove the serosa, and the exposed muscularis was abraded by rubbing 10 times with dry gauze. This cecal abrasion was left exposed for 15 minutes.

After 15 minutes of exposure, the anti-adhesion agent was introduced between the peritoneal defect and the cecal defect. The defects were placed in contact with each other, and the animals remained undisturbed for an additional 15 minutes. Then, using care to minimize disruption of the defects, the midline abdominal incision was closed with a running polypropylene suture. The skin was also closed with a running polypropylene suture. The animals were dressed and bandaged. All animals were housed individually.

Seven days following surgery, the animals were sacrificed and their abdomens examined for the presence of a peritoneal adhesion between the abdominal wall defect and the cecal defect.

The treated animals were divided into four groups (A through D). The animals in Groups A and D were treated with HA sponges prepared from a solution of unmodified HA ($1.2 \times 10^6$ daltons). The density of the HA sponges introduced into the Group A and Group D animals was 7.30 mg/cm$^2$ and 1.23 mg/cm$^2$, respectively. The animals in Group C were treated with an HA film prepared from a solution of unmodified HA ($1.2 \times 10^6$ daltons). The density of the HA film used in the Group C animals was 6.23 mg/cm$^2$. The animals in Group B were treated with a water-insoluble biocompatible sponge of the invention prepared according to the procedure described in Example 34 above. The density of the sponges used in the Group B animals was 1.26 mg/cm$^2$.
Results The incidence of adhesion formation was determined and compared between the treated animals and the untreated (control) animals. Seventeen untreated animals were divided into four control groups, and each control group had an equal number of animals as each test group. Each of the control animals developed an adhesion between the abdominal wall defect and the cecal defect. The validity of an agent being able to prevent the development of an adhesion was determined by statistical analysis of the reduction in incidence rate between treated and untreated animals.

As shown in Table I, the HA sponges used in Groups A and D were ineffective as anti-adhesion compositions because 100% of the animals developed adhesions between the defects.

The HA films used in Group C was only partially effective in adhesion prevention because 80% of those animals developed adhesions between the defects. The HA sponges prepared according to this invention, however, were completely effective in adhesion prevention because none of the animals in Group B developed adhesions between the defects.

TABLE I

| Group | device | density (mg/cm$^2$) | number of rats | % adhesion | standard deviation |
|---|---|---|---|---|---|
| A | sponge | 7.30 | 5 | 100% | 21.2 |
| B | sponge | 1.26 | 4 | 0% | — |
| C | film | 6.23 | 5 | 80% | 21.2 |
| D | sponge | 1.23 | 3 | 100% | 50.0 |

The foregoing description should be taken as illustrative and not limiting in any sense. Other embodiments of the invention will occur to those skilled in the art and are within the scope of the following claims.

What is claimed is:

1. A hyaluronic acid derivative formed by a method comprising the step of reacting hyaluronic acid with a biscarbodiimide.

2. The hyaluronic acid derivative of claim 1, wherein the biscarbodiimide has the formula:

$$R^1-N=C=N-R^2-N=C=N-R^3$$

and wherein $R^1$, $R^2$ and $R^3$ are each independently selected from the group consisting of hydrocarbyl, substituted hydrocarbyl, alkoxy, aryloxy and alkaryloxy.

3. The hyaluronic acid derivative of claim 1, wherein the molar equivalent of biscarbodiimide to hyaluronic acid is equal to or greater than 5%.

4. The hyaluronic acid derivative of claim 1, wherein the derivative is water insoluble.

5. The hyaluronic acid derivative of claim 1, wherein the derivative is biocompatible.

6. The hyaluronic acid derivative of claim 1, wherein the biscarbodiimide is p-phenylene bis-(ethyl)-carbodiimide.

7. The hyaluronic acid derivative of claim 6, wherein the molar equivalent of p-phenylene bis-(ethyl)-carbodiimide to hyaluronic acid is equal to or greater than about 12%.

8. The hyaluronic acid derivative of claim 1, wherein the biscarbodiimide is 1,6 hexamethylene bis-(ethyl)-carbodiimide.

9. The hyaluronic acid derivative of claim 8, wherein the molar equivalent of 1,6 hexamethylene bis-(ethyl)-carbodiimide to hyaluronic acid is about 18%.

10. The hyaluronic acid derivative of claim 1, wherein the derivative is in the form of a film.

11. The hyaluronic acid derivative of claim 1, wherein the derivative is in the form of a gel.

12. The hyaluronic acid derivative of claim 1, wherein the derivative is in the form of a sponge.

* * * * *